(12) United States Patent
Raber et al.

(10) Patent No.: US 6,376,550 B1
(45) Date of Patent: Apr. 23, 2002

(54) PHARMACEUTICAL COMPOSITIONS CONTAINING TRAMADOL FOR MIGRAINE

(75) Inventors: Marc Raber, Giessen; Helmut Momberger, Marburg, both of (DE)

(73) Assignee: ASTA Medica AG, Dresden (DE)

( * ) Notice: Subject to any disclaimer, the term of this patent is extended or adjusted under 35 U.S.C. 154(b) by 0 days.

(21) Appl. No.: 09/247,204

(22) Filed: Feb. 9, 1999

(51) Int. Cl.$^7$ .................. A61K 31/133; A61K 31/135; A61K 31/166
(52) U.S. Cl. ........................... 514/646; 514/619
(58) Field of Search ................... 514/646, 619

(56) References Cited

U.S. PATENT DOCUMENTS 5,437,874 A * 8/1995 Bru et al. ................ 424/466

FOREIGN PATENT DOCUMENTS

WO 9803179 * 1/1998

OTHER PUBLICATIONS

Zed et al., Ann. Pharmacother., 33(1), 66–72 (abstract), Jan. 1999.*

Nossol et al, Int. J. Clin. Prac., 52(2), 115–21 (abstract), 1998.*

Swain et al., South. Med. J., 90(9), 878–88 (abstract), 1997.*

Lee et al., Drugs, 46(2), 313–40 (abstract), 1993.*

Sahlender, H.M., Therapiewoche, 35(42), 4822–26 (abstract), 1985.*

Lee et al., Drugs, 46(2), pp. 313–40, 1993.*

* cited by examiner

Primary Examiner—Phyllis G. Spivack
(74) Attorney, Agent, or Firm—Goodwin Proctor LLP

(57) ABSTRACT

A method for treating migraine is disclosed in which a composition consisting essentially of pharmacologically effective amounts of both an antiemetic compound and tramadol is administered to a patient in need thereof.

6 Claims, No Drawings

PHARMACEUTICAL COMPOSITIONS CONTAINING TRAMADOL FOR MIGRAINE

FIELD OF THE INVENTION

The present invention relates to a new process for using pharmaceutical compositions containing tramadol, and an antiemetic-antinauseant substance for the treatment of migraines and migraine-like headaches.

BACKGROUND

Migraine is a disease with recurring attacks of headaches, which last between 4 and 72 hours. Migraine attacks predominantly are unilateral, dull at the beginning and then pulsing headaches occur with moderate to severe intensity. Typical accompanying symptoms of migraines are hypersensitivity towards light and sound, pallor, nausea and vomiting and without neurological focal attack, as a prodromal stage.

The (usual) migraine without aura is differentiated from the (classical) migraine with aura, which always commences with a characteristic scintillating scotoma. A complicated migraine exists if the visual disorders last for days or other neurological focal symptoms occur with the known special forms of the retinal, basilar, ophthal-moplegic, aphasic or hemiplegic migraine.

There are different ideas concerning the pathomechanism of the migraine. Earlier hemodynamic ideas, according to which the initial neurological attacks are triggered by regional, intracranial vasoconstriction and the subsequent pulsing headache by extracranial vasodilation with pain conduction over the nervus opththalmicus and nervus trigeminus, explain the processes during the migraine only inadequately.

The regional cerebral blood flow is reduced during a migraine with aura occipital, the slow migration of the cortical oligemia with crossing over of the supply regions of individual arteries suggesting that not only vasomotor, but also electrophysiological phenomena corresponding to the so-called "spreading depression" participating (Spierings ELH (1988); Recent advances in understanding of migraine. Headache 28; 655–658).

Other findings suggest that the accompanying headaches are triggered not only by an extracranial vasodilation, but also by a central lowering of the pain threshold, IEGs (immediate early genes) being activated in the cells of the spinal cord and of the brain stem after noxic stimulation (M. Zimmermann (1955); Neurobiology of the Pain System, Neuroforum 1/95; 34–45).

A different theory—the neurogenic inflammation model—offers a possibility of explaining the blood flow change as well as the increased pain sensitivity of the vessels during migraine attacks. According to this theory, the increased pain sensitivity is brought about by an increased sensitization of the sensory perivascular fibers of the trigeminovascular system. Vascular pulsations, which normally are not capable of initiating painful sensations, are potent pain stimuli due to this increased sensitization, and bring about the pulsing, throbbing migraine pain. The neurogenic inflammation is initiated by noxic stimulation of the perivascular nerve fibers of the meningeal blood vessels. From the nerve ends, which probably are nociceptors at the same time, neuropeptides such as P. neurokinin A and CGRP (calcitonin-gene related peptides), which are capable of initiating the neurogenic inflammation, are secreted. During a migraine attack, CGRP can also be detected in increasing amounts in the venous blood of the head.

A vicious circle is set in motion due to the secretion of the neuropeptides, wherein a peptide release leads to vasodilation and to an increase in capillary permeability, resulting in an increased stimulation of nociceptors which, in turn, leads to a yet increased release of peptides. The known antimigraine actives, such as sumatriptan and ergot alkaloids inhibit the release of the neuropeptides and interrupt the pain-initiating cycle (M. Zimmermann: Chronic Pain and its Causes, Deutsches Arzteblatt 93, vol. 43, 1996 A-2749–2752).

Other findings suggest a primary neurogenic hypothalamic dysfunction, during which the vasoactive serotonin, which is secreted in a reduced amount from the nuclei of the raphe of the brain stem during the migraine attack, plays a key role (Ferrari M D et al. (1989): Serotonin metabolism in migraine. Neurology 39: 1239–1242; R. Pramod et al. (1989): 5-$HT_1$-like receptor agonists and the pathophysiology of migraine. Trends in Pharmacological Sciences 10, 200–204).

Regardless of many hypotheses and complicated models, the patho-mechanisms of the migraine are not understood as yet. The migraine has a multifactorial genesis with a genetic disposition and external (such as alcohol) and internal (such as hormone) trigger mechanisms. It is not a psychosomatic disease, although psychic factors can trigger an attack.

Frequent side effects of ergotamine and dihydroergotamine which are the drugs of choice for treating migraines, are nausea, retching, vomiting, headaches, muscle pain and a general sensation of coldness. These are symptoms which, under a false assumption of a continuing migraine attack, may cause the compositions to be taken repeatedly and thus can lead to an overdosage. Persistent headaches may result from frequent use, and this fosters ergotamine abuse. Circulation disorders, coronary heart disease, occlusive arterial disease, hypertension and anginal disorders occur as serious side effects. Ergot alkaloids must not be used during pregnancy, while nursing or by children below the age of 12.

Sumatriptan and its derivatives (almotriptan, eletriptan, naratriptan, rizatriptan, zolmitriptan) are very effective migraine remedies which, when used orally, are superior to individual substances, such as ergotamine, acetylsalicylic acid or metoclopramide. Sumatriptan is contraindicated for children, during pregnancy, while nursing, and for patients above the age of 65 or having coronary heart disease. A sensation of pressure and heart, a general sensation of weakness, a sensation of tightness in the chest, hypertension, coronary heart disease, a myocardial infarction and angina pectoris can occur as undesirable effects.

Thus, although it has been known to combine some analgesics with antiemetics, these are either weak analgesics (e.g. paracetamol or salicylates) that are not useful against moderate to severe migraine pain. Strong analgesics, such as ergot compounds or sumatriptan, are unreliable, because they are known to have adverse cardiac and other undesirable side effects, and also to cause nausea.

Metoclopramide and domperidone have been used in combination with ergot compounds because of their prokinetic effects, and also because of their effect on symptoms such as nausea and vomiting, which frequently occur as symptoms that accompany a migraine.

The medicinal treatment of migraines is symptomatic in nature and does not represent a cure. Mixed preparations of non-opioid analgesics and mixed preparations of ergot alkaloids are not recommended, since they themselves can cause headaches when used for a prolonged period and particularly when used daily. Furthermore, liver and kidney damage, such as analgesic nephropathy are possible consequences of the long-term use of analgesic combination. Because of the possibility that they will be misused or result in dependence, opioid analgesics are generally not suitable for the treatment of migraines.

The following specific combinations, in particular, are known from the patent literature for the treatment of migraines: paracetamol and metoclopramide (EP 011 489, EP 011 490, U.S. Pat. No. 5,437,874, EP 695 546, EP 774 253); acetylsalicylic acid or the 1-lysine derivative thereof and metoclopramide (EP 605 031); and analgesics (such as acetylsalicylic acid), antiemetics (such as metoclopramide) and an antacid (CA 20 20 018). The above analgesic combinations are generally suitable for the treatment of mild migraine attacks. They are not suitable, however for the treatment of moderately severe to severe migraines. In the case of severe migraines, ergot alkaloids, in combination with an antiemetic or sumatriptan, are generally indicated.

It is a disadvantage that, under treatment with ergot alkaloids or sumatriptan, a large number of, in some cases, serious cardiovascular side effects, such as angina pectoris, coronary heart disease, hypertension and myocardial infarction can occur.

An alternative class of analgesics, the opioid analgesics are generally also unsuitable for such use, partly because of their dependence-creating effect, and also their tendency to cause constipation which works against the desired fast analgetic effect.

Tramadol is a centrally acting analgesic having a weak opioid binding activity and a complimentary weak inhibition of reuptake of norepinephrine and serotonin. Unlike morphine, tramadol does not show a histamine release. It was, however, not considered to be used in preference to opioids, because it is known to cause nausea, vomiting, sweating, dryness of the mouth, dizziness and drowsiness can occasionally occur. Gastrointestinal complaints or different types of mental effects are infrequently also observed. Therefore, tramadol has not been successfully used against migraine pain.

WO 97/18801 describes the combination of tramadol with antinauseant substances, particularly in a controlled release dosage form. There is, however, no prior suggestion of using such combinations for the treatment of migraines.

There is therefore a great need for a reliable analgesic, which has few side effects and a good activity in the case of moderately severe to severe migraine attacks.

SUMMARY OF THE INVENTION

It is an object of the present invention to prepare an improved therapeutic agent for the treatment of moderately severe to severe migraine attacks.

The present invention is a composition containing tramadol and an antiemetic antinauseant substance, including dopamine antagonists, phenothiazine, 5HT$_3$ antagonists, and antihistamines (hereinafter singly and collectively referred to as "antiemetics"). It has been surprisingly found that in accordance with the present invention tramadol was also found to be an exception among opioid analgesics, which does not produce the serious side effects which are typically seen in the use of opioids. Not only is the constipation-causing side effect of opioid analgesics effectively suppressed by combining tramadol with such an antiemetic, but additionally the analgesic action is also unexpectedly potentiated by the antiemetic, and the absorption and compatibility of tramadol is increased by the combination of the present invention. Yet further analgesic activity can be provided by a further combination with one or more conventional analgesics, such as an NSAID, thus also to provide an antiinflammatory effect.

As used throughout the specification and the claims, "tramadol" means 2-[(dimethylamino)methyl]-1-(3-methoxyphenyl)cyclohexanol, or its pharmaceutically acceptable salts, esters, and enantiomers. Tramadol is an analgesic, which is pharmacologically effective in the case of moderately severe to severe pain. It belongs to the group of opioids with a weak activity. In comparison to other opioids, tramadol is distinguished by a lesser development of tolerance with respect to the analgesic effect and by the fact that the side effects, typical of an opiate, are largely absent and that the potential for developing a dependence is very slight. The analgesic effect of tramadol includes opioid as well as non-opioid components, the latter by way of the release of serotonin (5-HT) and the inhibition of the resorption of serotonin and noradrenalin in the central nervous system (CNS). These non-opioidal components provide a significant contribution to the analgesic effect of tramadol. Noradrenaline resorption is inhibited predominantly by the (−)-enantiomer and the release of serotonin, as well as the inhibition of the resorption of serotonin from the synaptic cleft is produced predominantly by the (+) enantiomer. Both enantiomers contribute to the analgesic effect in man.

As used throughout the specification and the claims, compounds the main representatives of which include metoclopramide, domperidone, prochlorperazine, trifluoroperazine, promethazine, dimenhydrinate, cinnarizine, cyclizine, ondansetron, granisetron, and tropisetron, in addition to their role as antiemetics in the present invention, also potentiate the analgesic efficacy of tramadol. They are also pharmacologically active to increase the tonus of the lower gastroesophageal sphincter and to stimulate and accelerate the emptying of the stomach and the passage through the small intestine, which emptying is otherwise disturbed or otherwise hindered by the migraine, and also as antiemetics to suppress nausea, retching and vomiting. The antiemetics are conventionally also indicated in the case of gastroparesis, which can occur postoperatively, and also in the case of some basic diseases (such as diabetes mellitus, etc.). They are also given in the case of functional dyspepsia (irritated stomach), as the cause of the latter is suspected to be a disorder of gastrointestinal motility. Any reference in the disclosure and the claims to an "antiemetic" is meant to include its pharmaceutically acceptable salt and esters.

It was noted with surprise that, as a result of the use of the combination of tramadol and an antiemetic, the migraine attacks can be effectively cut short and the occurrence of nausea and vomiting are be prevented. This was all the more surprising, since tramadol itself can cause nausea and vomiting or intensify these symptoms that accompany migraines. For this reason, tramadol was regarded in the past as being unsuitable as a sole active for the treatment of migraines.

By combining tramadol with an antiemetic, most suitably with metoclopramide, it is possible to make the more highly effective analgesic tramadol available for the treatment of moderately severe to severe pain, including the treatment of migraines. With the combination of the present invention the compatibility of tramadol can be improved, the absorption of tramadol in the gastrointestinal tract can be accelerated and the occurrence of accompanying symptoms of migraines, namely nausea and vomiting, can be prevented.

Tramadol and antiemetics, are also suitable as partners in using these compositions from the point of view of their pharmacodynamic and pharmacokinetic properties. The duration of the analgesic effect of tramadol is about 4 to 7 hours, with a terminal elimination half life of about 5–6 hours. The duration of the prokinetic effect of e.g. metoclopramide and domperidone is about 1 to 2 hours and that of the antiemetic effect about 3 to 5 hours. The half life time is about 4 to 6 hours.

In a further embodiment of the process of the present invention, the combinations can additionally be used with suitably from about 1% wt. to about 15% wt. of a non-steroidal antiinflammatory drug (NSAID) such as acetylsalicylic acid, ibuprofen, naproxen and paracetamol. By these means, on the one hand, a different analgesic mechanism is created by an effect of tramadol on the central nervous system, and the analgesic and antiinflammatory effect of non-steroidal antiinflammatory drugs on both the central and peripheral nervous systems. Therefore, these combinations with an NSAID can be of particular importance in the case of therapy-resistant forms of migraines. On the other hand, the total dose of tramadol or of the additional combination partner having analgesic activity can be reduced without loss of effect on the pain, without undesirable side effects such as gastrointestinal disorders in the case of the NSAIDs.

The composition of the present invention can be administered in any suitable dosage form such as tablets, effervescent tablets, capsules, granulates, powders, sustained release tablets, sustained release capsules (single and multiple unit formulations), ampoules for intravenous and intramuscular injection and in the form of infusion solutions, suspensions, suppositories or in any other suitable dosage form.

The sustained release dosage forms of the present invention can contain the active ingredient completely or partly in the sustained release form with or without an initial, immediate dosing of the actives.

The active ingredients can be present jointly or partially or completely in separate formulations, so that it is possible to administer them separately as well as at different times. If the active ingredients are present only in separate formulations, these formulations are suitably matched to one another and each contains a respective active ingredient within the dosage unit in the same amounts and corresponding ratios by weight, in which they can and would be present in a combined dosage form. The active ingredients can also be present in the form of their pharmaceutically usable salts in any of these pharmaceutical dosage forms. Oral pharmaceutical compositions, dosage forms which contain a combination of the actives, are deemed to be most suitable.

Pharmaceutical preparations containing these combinations in their given amounts, are suitably formulated with physiologically compatible carriers and/or diluents and/or inactive ingredients in the desired manner. Examples of carriers and inactive ingredients include gelatin, natural sugars such as cane sugar or lactose, lecithin, pectin, starch (such as corn starch or amylose), cyclodextrins and cyclodextrin derivatives, dextran, polyvinylpyrrolidone, polyvinyl acetate, gum arabic, alginic acid, tylose, talcum, lycopodium, silica, calcium hydrogen phosphate, cellulose, cellulose derivatives such as methyloxypropyl cellulose, methyl cellulose, hydroxypropylmethyl cellulose, hydroxypropylmethyl cellulose phthalate, $C_{12-22}$ fatty acids, emulsifiers, oils and fats, particularly also vegetable glycerin esters and polyglycerin esters of saturated fatty acids, monohydric or polyhydric alcohols and polyglycols, such as polyethylene glycols, esters of aliphatic saturated or unsaturated $C_{2-22}$ fatty acids with monohydric, $C_{1-20}$ aliphatic or polyhydric alcohols, such as glycols, glycerin, diethylene glycol, 1,2-propylene glycol, sorbitol, and mannitol.

Further inactive ingredients can suitably include materials, which bring about disintegration (so-called disintegrants), crosslinked polyvinylpyrrolidone, sodium carboxymethyl starch, sodium carboxymethyl cellulose and microcrystalline cellulose. Known coating agents can likewise be used. Polymers, as well as copolymers of acrylic acid and/or methacrylic acid and/or their esters, zein, ethylcellulose, ethylcellulose succinate and shellac are particularly suitable.

As plasticizers for coatings, citrate and tartrate esters, glycerin and glycerin esters and polyethylene glycol of different chain lengths can be used. Water or physiologically compatible organic solvents, such as alcohols and fatty alcohols, can be suitably employed for the preparation of solutions or suspensions.

For liquid preparations, it may be necessary to use preservatives, such as potassium sorbate, methyl-4-hydroxy benzoate or propyl 4-hydroxybenzoate, antioxidants, such as ascorbic acid, and a taste improver such as peppermint oil.

Customary solubilizers or emulsifiers, such as polyvinylpyrrolidone and polysorbate 80 can be used in preparing the compositions. Further examples of carriers and inactive ingredients include those described, for example in H. P. Fiedler "Lexikon der Hilfsstoffe für Pharmazie, Kosmetik und Angrenzende Gebiete (Encyclopedia of Inactive Ingredients for Pharmaceuticals, Cosmetics and Adjoining Fields)".

Anti-migraine preparations, which contain the combinations of antiemetics with prokinetic effect and of tramadol, the composition can suitably contain from about 5% wt. to about 30% by weight of the antiemetic. Suitably the weight ratio of the compounds is from about 1:4 to about 1:10. Individual doses of these pharmaceutical preparations can contain from about 5 to about 50 mg of an antiemetic, and from about 50 to about 400 mg of tramadol. Moreover, the daily dose should suitably contain from about 20 to about 80 mg of antiemetic and from about 200 to about 400 mg of tramadol. Depending on the therapeutic indication, the daily dose can be administered all at once, or in the form of from about 2 to about 4 partial doses per day. In general, the administration in from about 2 to about 4 partial doses per day is most suitable.

The following examples exemplify the invention in further detail.

EXAMPLE 1

Preparation of a Metoclopramide Solution

Purified water (802.4 g) is added to a suitable container, and 4.7 g of metoclopramide hydrochloride $1H_2O$, 0.1 g of ascorbic acid, 170.1 g of sorbitol, 2.8 g of potassium sorbate and a pre-dissolved solution of 18.9 g of 96% ethanol (v/v), 0.7 g of methyl 4-hydroxybenzoate and 0.3 g of propyl 4-hydroxybenzoate are added with stirring, with the stirring continued until all the components are dissolved. The solution is filtered through a suitable filter.

| Formulation | Percentage (w/w) |
| --- | --- |
| metoclopramide hydrochloride. $H_2O$ | 0.47 |
| ascorbic acid | 0.01 |

-continued

| Formulation | Percentage (w/w) |
|---|---|
| sorbitol | 17.01 |
| potassium sorbate | 0.28 |
| 96% ethanol (v/v) | 1.89 |
| methyl 4-hydroxy benzoate | 0.07 |
| propyl 4-hydroxybenzoate | 0.03 |
| purified water | 80.24 |

The solution is filled into a suitable dropper bottle.

EXAMPLE 2

Preparation of a Metoclopramide Solution

Purified water (484.2 g) is added to a suitable container and 100 g of metoclopramide hydrochloride, 1.5 g of potassium sorbate, 161.8 of 96% ethanol (v/v), 124.5 g of 1,2-propylene glycol, 200 g of refined sugar, 1.0 g of polysorbate 80 and 1.0 g of peppermint oil are added with stirring, the stirring being continued until all the components are dissolved. The solution is filtered through a suitable filter.

| Formulation | Percentage (w/w) |
|---|---|
| tramadol hydrochloride | 9.3 |
| potassium sorbate | 0.1 |
| 96% ethanol (v/v) | 15.1 |
| 1,2-propylene glycol | 11.6 |
| refined sugar | 18.6 |
| polysorbate 80 | 0.1 |
| peppermint oil | 0.1 |
| purified water | 45.1 |

The solution is filled into a suitable dropper bottle.

EXAMPLE 3

Sustained Release Tramadol—Metoclopramide Pellets

Preparation of Active Ingredient-containing Cores

A tramadol hydrochloride/metoclopramide hydrochloride 1H$_2$O/Aerosil® 200 mixture (4824 g) is applied with approximately 2200 g of a 15% solution of ethylcellulose/shellac (6:4) in approximately 96% ethanol (v/v) on 1000 g of neutral pellets of a suitable size (with a diameter, for example, of between 0.5 and 0.6 mm) in a coated-tablet kettle. The cores obtained were subsequently dried and screened (0.8–1.4 mm).

Application of the Membrane

A membrane is applied on 6.15 kg of the active ingredient-containing cores, so prepared, in that 470 g of a 15% solution of ethylcellulose/shellac (6:4) in 96% ethanol (v/v) are applied. Talcum (700 g) is powdered in as release agent.

| Formulation | Percentage (w/w) |
|---|---|
| tramadol hydrochloride | 57.8 |
| metoclopramide hydrochloride. H$_2$O | 11.6 |
| neutral pellets | 14.4 |
| ethylcellulose | 3.5 |
| shellac | 2.3 |
| Aerosil 200 | 0.3 |
| talcum | 10.1 |
| 96% ethanol (v/v) | to volume |

Release of Active Ingredient

The in vitro release of tramadol hydrochloride from the sustained release pellets of the example is determined by the method of USP 23/NF 18 in Apparatus 3. The temperature of the release medium is 37° C., the sample tubes are lifted at the rate of 20 lifts per minute and the amount of test solution per test interval is 175 mL.

The investigation is commenced with the test solution at a pH of 1.5. After the first hour, the tubes with the samples are changed in 175 mL of test solution at pH 4.5, after the second hour in a test solution at pH 6.9, after the fourth hour in a test solution at pH 6.9, after the sixth hour in a test solution at pH 7.2 and, after the eight hour, in a test solution of pH 7.5. The amount of active ingredient, released into the solution medium at the aforementioned times, is determined spectrophoto-metrically. The following release values are determined for tramadol hydrochloride.

| Time - hours | Percentage by weight of active ingredient released |
|---|---|
| 1 | 39 |
| 2 | 57 |
| 4 | 70 |
| 6 | 78 |
| 8 | 84 |
| 12 | 93 |

The in vitro release curve of the sustained release pellets is shown in FIG. 1.

EXAMPLE 4

Tramadol—Metoclopramide Capsules

Preparation of the Filling Composition for the Capsules

Tramadol hydrochloride (323 g), 6.5 g of metoclopramide hydrochloride. H$_2$O, 597 g of calcium hydrogen phosphate, 0.5 g of colloidal silica sold under the trademark Aerosilr® 200, and 1.0 g of magnesium stearate are screened and mixed in a suitable mixer.

| Formulation | Percentage (w/w) |
|---|---|
| tramadol hydrochloride | 32.3 |
| metoclopramide hydrochloride. H$_2$O | 6.5 |
| calcium hydrogen phosphate | 59.7 |
| Aerosil ® 200 | 0.5 |
| magnesium stearate | 1.0 |

Preparation of the Capsules

The filling composition for the capsules (155 mg nominally) is filled by means of a suitable machine into hard gelatin capsules of suitable size.

EXAMPLE 5

Drink-producing Tablets

A powder blend was prepared from 251 g tramadol-HCl, 25 g metoclopramide-HCl.H$_2$O, 4 g Aerosil™ 200, 50 g Aspartame™, 100 g crospovidone, 700 g microcrystalline cellulose, 819.5 lactose monohydrate, 37.5 g flavoring (e.g. strawberry), 10 g sodium dodecyl sulfate, and 3 g magnesium stearate. The ingredients were screened and mixed in a blender.

| Formula | Percentage (w/w) |
|---|---|
| tramadol-HCl | 12.55 |
| metoclopramide-HCl.H$_2$O | 1.25 |
| Aerosil ™ 200 | 0.2 |
| Aspartame ™ | 2.5 |
| crospovidone | 5.0 |
| microcrystalline cellulose | 35.0 |
| lactose monohydrate | 40.0 |
| flavoring | 1.88 |
| sodium dodecyl sulfate | 0.5 |
| magnesium stearate | 0.15 |

The powder blend was compressed into tablets (nominally 400 g each).

EXAMPLE 6

Treatment of Migraines with Tramadol/metoclopramide

Patients were treated for medium to intensive migraine attacks which could no longer be satisfactorily treated with weaker NSAID analgesics, such as acetylsalicylic acid, ibuprofen, or paracetamol.

The intensity of the migraine headaches and the marked accompanying symptoms that were present prior to treatment, were documented to obtain a baseline for the evaluation of the treatment results. The intensity of pain before and after administration of the treatment were recorded on a 100 mm long VAS scale and were determined 30 mins., and then 1, 2, 4, 6 and 12 hours later. The noting of the effects that accompanied the migraine headaches, and their changes after administration of the drug treatment were recorded on a plural step verbal rating scale. The patient's general subjective impressions were also recorded.

Eight patients (7 female and 1 male) with an average age of 44.7 years (between ages 35 and 63), an average height of 169.3 cm (between 159 and 186 cm), and an average body weight of 70.4 kg (between 55 and 103 kg), were treated.

All patients satisfied the operational and diagnostic criteria of the IHS for the diagnosis of migraines and have had at least 5 migraine attacks lasting 4–72 hours prior to the commencement of the treatment. The headaches were strongly along one side, and their intensity was exacerbated by bodily activity. All of the patients were nauseous, and sensitive to noises during their attacks. 28% of the patients also had vomiting episodes, and 43% were sensitive to light. The migraines have preexisted in the average since 15.3 years (between 2 and 38 years), and the mean frequency of attacks was 4.1 days per month (between 2 and 8 days per month).

During the test period of 4 months the patients suffered 11 acute migraine attacks which were treated with a free combination of tramadol and metoclopramide. All patients were administered an oral single dose of 100 mg tramadol (2 tramadol capsules sold by Arzneimittelwerk Dresden, each containing 50 mg tramadol-HCl), and 10 mg metoclopramide solution (30 drops of metoclopramide sold by Temmler, in 5 mg solution).

Before the documented treatments, the migraine pains of the patients were characterized as from intensive to very intensive. The initial pain as a mean value on the VAS scale was 75±7 mm (between 62 and 83 mm).

The pains of two patients who each were treated for two migraine attacks during the 4 month test period, did not result in any improvement in their conditions, and were declared to be nonresponsive to the treatment, and were excluded from the analysis of the test results. The remaining 6 patients were treated for 7 attacks during the test period. Their headaches were recorded on the same 100 long VAS scale which was also customarily used for other pain studies.

The headaches were evaluated on the following basis:

| | | |
|---|---|---|
| 0 mm | no headaches | (stage 0) |
| 1–30 mm | light headaches | (stage 1) |
| 31–60 mm | medium heavy headaches | (stage 2) |
| 61–100 mm | strong to very strong headaches | (stage 3) |

In migraine studies the criteria for results are determined as the percentage of patients in the case of which an improvement of their headache (from stage 3 to stage 2, or stage 1 or stage 0) is obtained within a predetermined time period (usually after 2 or 4 hours).

The results are summarized in the following table which shows for the tramadol/metoclopramide responding patients the differences between the intensities of their initial headaches measured on the VAS scale at 30 mins., and 1, 2, 4, 6, and 12 hours after administration of 100 mg tramadol and 10 mg methoclopramide (with the values within parentheses showing the change in headache intensity).

| Patient | 0 h mm | 0.5 h mm | 0.5 h % | 1 h mm | 1 h % | 2 h mm | 2 h % | 4 h mm | 4 h % | 6 h mm | 6 h % | 12 h mm | 12 h % |
|---|---|---|---|---|---|---|---|---|---|---|---|---|---|
| VS | 62 | −2 | (−3.2) | −14 | (−22.6) | −24 | (−38.7) | −27 | (−43.6) | −28 | (−45.2) | −62 | (−100) |
| KM | 83 | −19 | (−22.9) | −42 | (−50.6) | −60 | (−72.3) | −61 | (−73.5) | −45 | (−54.2) | −43 | (−51.8) |
| VS | 81 | 2 | (2.5) | −9 | (−11.1) | −21 | (−25.9) | −37 | (−45.7) | −81 | (−100) | −81 | (−100) |
| CM | 70 | −37 | (−52.9) | −37 | (−52.9) | −38 | (−54.3) | −30 | (−42.9) | −30 | (−42.9) | −29 | (−41.4) |
| SS | 72 | −6 | (−8.3) | −32 | (−44.4) | −87 | (−93.1) | −70 | (−97.2) | −72 | (−100) | −72 | (−100) |
| MK | 80 | −70 | (−87.5) | −65 | (−81.3) | −59 | (−73.8) | −45 | (−56.3) | −80 | (−100) | −80 | (−100) |
| RH | 77 | 2 | (2.8) | 1 | (1.3) | * | * | −77 | (−100) | −77 | (−100) | −77 | (−100) |
| Mean | 75 | −18.57 | (−24.25) | −28.29 | (−37.36) | −38.43 | (−51.15) | −49.67 | (−86.58) | −59 | (−77.46) | −63.43 | (−84.75) |
| Std. dev. | 7 | 28.68 | (34.04) | 22.58 | (28.27) | 24.81 | (31.97) | 19.88 | (25.94) | 23.88 | (28.32) | 20.19 | (26.22) |

The following table additionally summarizes the treatment results on a percentage basis showing the improvement in the headache degree staging from 3 to 2 or to 1 or 0, as a function of time after oral application of 100 mg tramadol and 10 mg metoclopramide solution.

| Time (hours) | No. of patients (n = 8) | Improvement from Stage 3→2 to 1→0 (% patients) |
|---|---|---|
| 0,5 | 2 | 25 |
| 1 | 5 | 62 |
| 2 | 6 | 75 |
| 4 | 6 | 75 |
| 6 | 6 | 75 |
| 12 | 6 | 75 |

The headaches have improved on the average after administration of the free combination of tramadol and metoclopramide in the group of the patients responding to treatment, within already 30 mins by 24.3%, and after 2 hours by 51.1%, related to the starting pain. After 4 and 6 hours, respectively, the reduction in pain intensity was on the average 65.6% and 77.5% (See the first Table).

For the entire group of patients, including the non-responders, an efficacy (improvement of headaches from strong or medium strong to light or pain-free) of 25% was obtained after 30 minutes, and 75% after 2 hours (see the second Table).

The foregoing data show that the tramadol/metoclopramide combination is a much more promising agent for the treatment of moderate or strong acute migraine headaches than e.g. NSAIDs, ergotamine preparations, triptanes and other mixtures.

We claim:

1. A process for treating migraine, which comprises administering to a patient in need thereof a composition having an active ingredient consisting essentially of a pharmaceutically effective amount of both an antiemetic and tramadol.

2. The process of claim 1, wherein said antiemetic compound is chosen from the classes of dopamine antagonists, phenothiazines, $5HT_3$ antagonists, and antihistamines.

3. The process of claim 2, wherein the dopamine antagonists are metoclopramide and domperidone, the phenothiazines are prochlorperazine and promethazine, the antihistamines are dimenhydrinate, cinnarizine and cyclizine, and the $5HT_3$ antagonists are ondansetron, granisetron and tropisetron.

4. The process of claim 1, wherein said pharmacologically effective amount of said antiemetic compound is between from about 5% wt. to about 30% wt. calculated as the anhydrous antiemetic.

5. The process of claim 4, wherein said pharmacologically effective amount of said tramadol is from about 75% wt. to about 90% wt. calculated as anhydrous tramadol.

6. The process of claim 1, wherein said pharmacologically effective amount of said tramadol is from about 75% wt. to about 90% wt. calculated as anhydrous tramadol.

* * * * *

UNITED STATES PATENT AND TRADEMARK OFFICE
CERTIFICATE OF CORRECTION

PATENT NO.     : 6,376,550 B1
DATED          : April 23, 2002
INVENTOR(S)    : Marc Raber and Helmut Momberger It is certified that error appears in the above-identified patent and that said Letters Patent is hereby corrected as shown below:

<u>Title page,</u>
Item [60], insert:
-- This is a nonprovisional application based on provisional application No. 60/075,332 filed on February 20, 1998. --

Signed and Sealed this

First Day of October, 2002

Attest:

Attesting Officer

JAMES E. ROGAN
*Director of the United States Patent and Trademark Office*